United States Patent
Dörnhöfer et al.

[11] Patent Number: 6,007,530
[45] Date of Patent: Dec. 28, 1999

[54] ANGIOPLASTY CATHETER FOR EXPANDING AND/OR OPENING UP BLOOD VESSELS

[75] Inventors: Thomas Dörnhöfer, Karlsbad; Burkhard Husslein, Karlsruhe; Christian Meyer, Walzbachtal; Erhard Starck, Kelkheim; Harry Zscheeg, Heidelberg, all of Germany

[73] Assignee: C.R. Bard, Inc., Murray Hill, N.J.

[21] Appl. No.: 08/894,722

[22] PCT Filed: Feb. 9, 1996

[86] PCT No.: PCT/EP96/00553

§ 371 Date: Jan. 26, 1998

§ 102(e) Date: Jan. 26, 1998

[87] PCT Pub. No.: WO96/24297

PCT Pub. Date: Aug. 15, 1996

[30] Foreign Application Priority Data

Feb. 9, 1995 [DE] Germany ............................ 195 04 261

[51] Int. Cl.⁶ .............................. A61B 17/00; A61M 5/14
[52] U.S. Cl. .................................. 606/1; 604/22
[58] Field of Search ................. 606/1, 169, 171; 600/439, 466, 462; 604/22

[56] References Cited

U.S. PATENT DOCUMENTS

| | | |
|---|---|---|
| 4,870,953 | 10/1989 | Donmichael ............................ 606/1 X |
| 5,197,946 | 3/1993 | Tachibana ................................. 604/22 |
| 5,209,719 | 5/1993 | Baruch et al. ............................. 604/22 |
| 5,375,602 | 12/1994 | Lancee et al. ............................ 600/439 |
| 5,423,797 | 6/1995 | Adrian et al. . |
| 5,569,179 | 10/1996 | Adrian ...................................... 604/22 |

FOREIGN PATENT DOCUMENTS

| | | |
|---|---|---|
| 0 423895 A1 | 4/1991 | European Pat. Off. . |
| 2 645 009 | 10/1990 | France . |
| 33 20 076 C2 | 12/1984 | Germany ...................... A61M 25/00 |
| 40 12 649 A1 | 10/1991 | Germany ...................... A61M 29/00 |
| 92 01 510 U | 3/1993 | Germany . |
| 3439 434 A1 | 4/1996 | Germany . |

Primary Examiner—Michael Buiz
Assistant Examiner—Vikki Trinh
Attorney, Agent, or Firm—Darby & Darby

[57] ABSTRACT

The invention pertains to an angioplasty catheter for expanding and/or opening up morbidly constricted or obstructed blood vessels, comprising at least one rotor (3) that is rotatively mounted in a cylindrical housing (4) at the distal end of the catheter, is connected to a rotational actuator (2) and is guided in the axial and/or radial direction along a preset path of motion (5), where as a result of the guided motion, the turning rotor (3) mechanically generates endogenous sound waves, especially sound waves in the ultrasound range, and induces a corresponding motion of the housing (4).

14 Claims, 4 Drawing Sheets

Section A-A

Section A-A

Fig. 1a
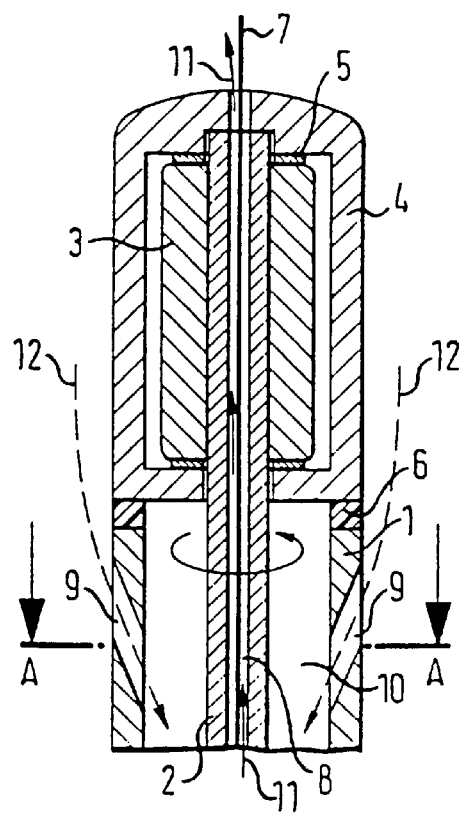
Fig. 1b
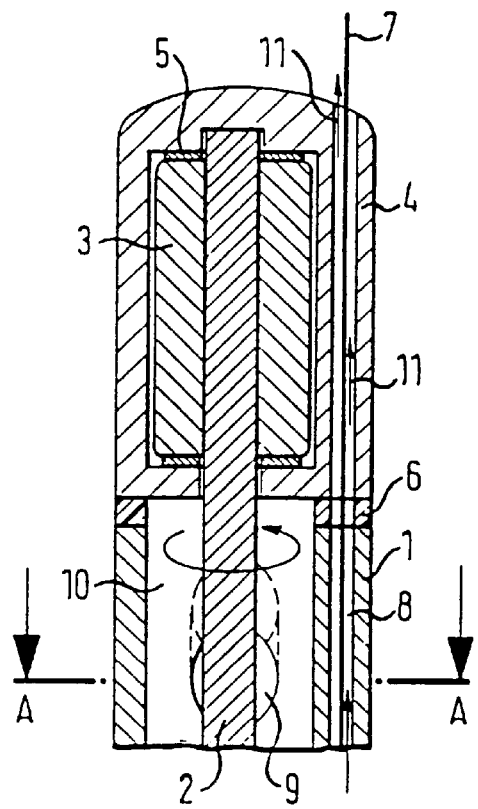
Section A—A
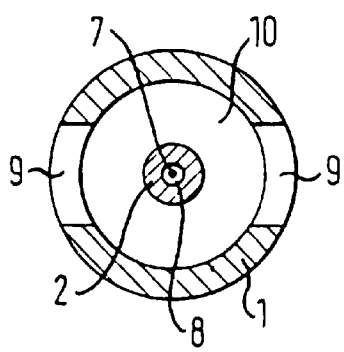
Section A—A
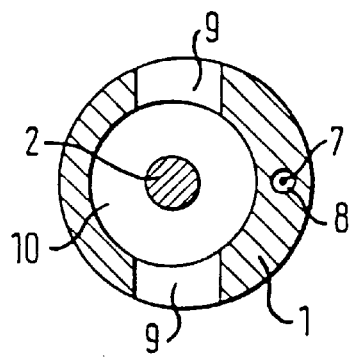

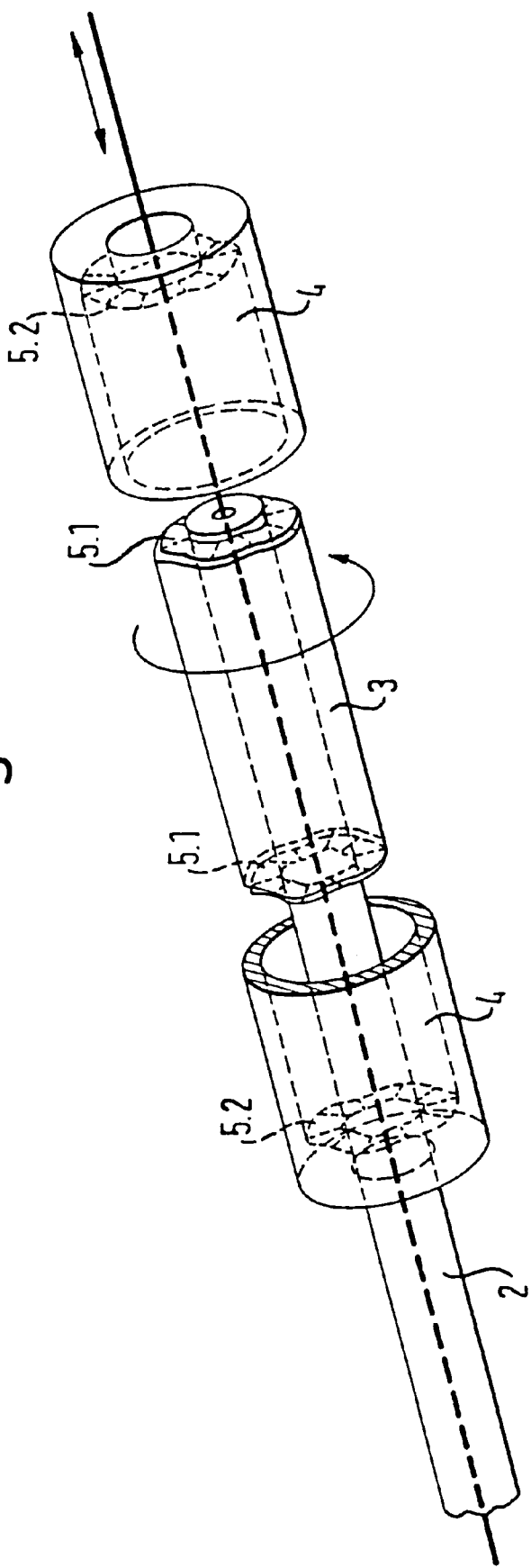

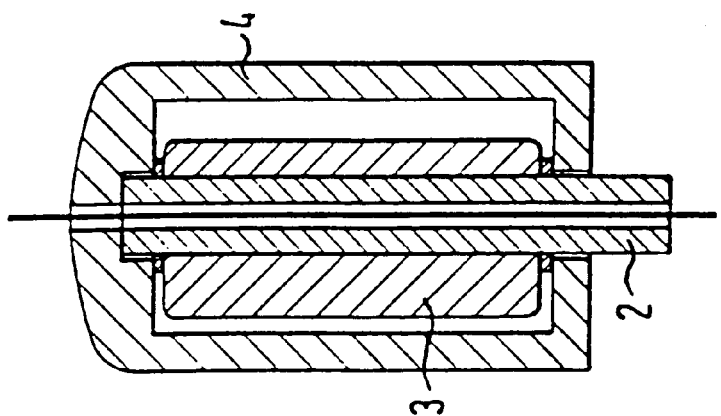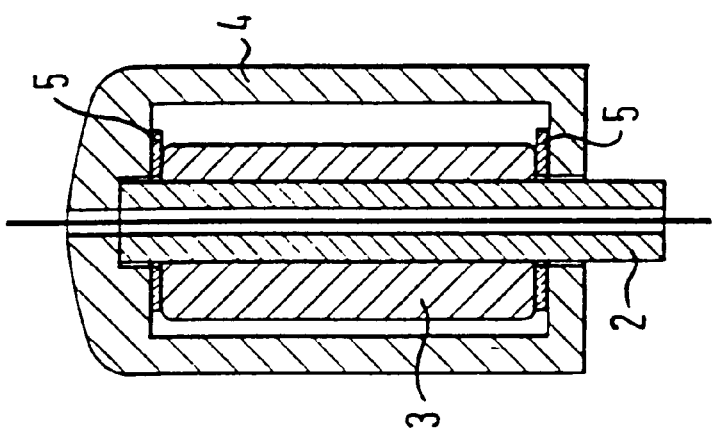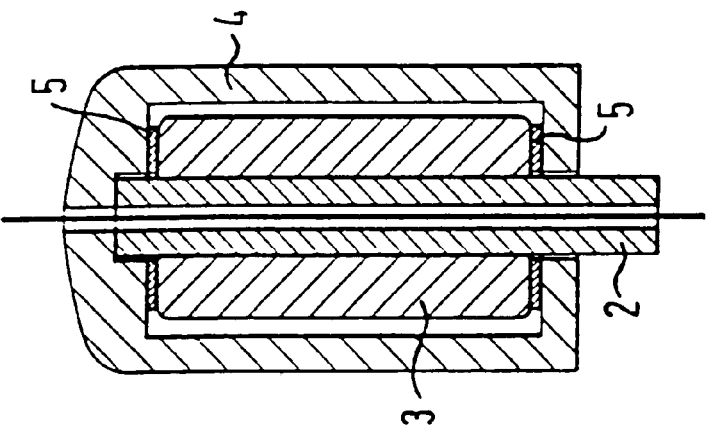

ANGIOPLASTY CATHETER FOR EXPANDING AND/OR OPENING UP BLOOD VESSELS

The invention relates to an angioplasty catheter for expanding and/or opening up morbidly constricted or obstructed blood vessels.

The invention also relates to a method of generating sound waves, particularly ultrasonic waves, within an angioplasty catheter.

The techniques, as known in medical technology, for expanding or recanalizing morbidly changed arteries are usually extremely invasive, e.g. balloon-tipped catheters, rotablators and Kensey catheters, or they are only used for the narrow-lumen recanalization of occlusions and have to be applied in combination with subsequent balloon dilation. The resultant trauma is the origin of renewed occlusion. A high relapse rate results therefrom.

For this reason, medical technology has switched over to the application of so-called ultrasonic recanalization techniques by means of which this risk of trauma can be minimized and hence the relapse rate significantly reduced. Ultrasonic recanalization is consequently a gentle technique for treating morbid arterial changes, with minimal traumatization of the vascular wall as a result of the selective ultrasonic effect. This is proved in the literature by in vivo and in vitro experiments.

A system in which the exogenously generated ultrasound is intra-arterially supplied to the stenosis or occlusion via a wire probe sheathed by a protective catheter is known from U.S. Pat. No. 4,870,953. The relatively inflexible wire probe which is difficult to control can be used only in a few vascular areas. A controlled release of energy is not possible either as a result of the long transmission distance encountered in intra-arterial applications.

An injection instrument in which a piezoceramic ultrasonic transducer is located at the distal end of the catheter is known from U.S. Pat. No. 5,197,946. The acoustic power of this ultrasonic transducer is, however, sufficient only to distribute injected medication and to boost and accelerate the effect of lysis medication. The released acoustic power is, nevertheless, too low for an effective ablation of for example the material of a vasoconstriction.

A rotating dilation catheter in which a stylet is inserted as a support and control element inside the inner lumen of a tubular wire coil with at least one pressure body is known from DE-OS 40 12 649 A1. This instrument is intended to be used to compact tissue in the stenosis in a radially outward manner and to smooth the inner vascular wall. To ensure a gentle application, the instrument can be used only in a slowly rotating manner, perhaps up to several thousand revolutions per minute. Technically speaking, this dilation catheter therefore cannot be used to generate ultrasound and this application is not envisaged either. The treatment principle also aims at displacement rather than the separation or disintegration of occlusive material.

A catheter in which a rotating removal instrument, i.e. a rotating miniature tool such as a cutter, drill etc., is used for therapeutic purposes is known from DE 33 20 076 C2. The rotational forces needed to drive these tools are generated by a probe tip designed as a fluid turbine and having tangential nozzles. The use of these tools causes the system to exhibit extremely invasive action, thus involving the aforementioned risks of embolization as a result of separating fairly large connected particles as well as the risk of damaging healthy tissue and a high re-occlusion rate conditioned thereby.

The invention is consequently based on the object of providing a simple and effective angioplasty catheter that is in turn based on the sound wave principle and designed for treatment of morbidly changed blood vessels; application of this catheter causes as little traumatization of the vascular walls as possible and hence permits maximum long-term treatment success rates. Another object of the invention is to provide a suitable and effective method of generating sound waves, particularly ultrasonic waves, in an angioplasty catheter.

This object is solved by an angioplasty catheter according to the invention and comprising the features of claim 1.

This angioplasty catheter comprises at least one rotor rotatably disposed within a cylindrical housing at the catheter's distal end, force-guided on a predetermined track of motion in an axial and/or radial direction and connected to a rotary drive, whereby as a result of the force-guided motion, the rotating rotor generates in a mechanically endogenous manner sound waves, particularly sound waves in the ultrasonic range, and induces a corresponding motion of the housing. It should be noted that the cylindrical housing need not necessarily be completely closed, but may also be designed as a cage-like structure with bar-shaped or mesh-like lattices etc. In the case of the aforementioned versions, all the rotating parts are encased such that no rotational motion is transferred to the biological tissue. The rotor is preferably made of hard metal or an extremely wear-resistant ceramic and the cylindrical housing is preferably made of steel. In principle, other suitable materials are of course conceivable as well. Due to the forced guidance according to the invention and on the basis of preferably high rotor speeds, the catheter's moving parts, particularly the rotor and any components in direct contact therewith, are subjected to extremely high loads and considerable wear. But since normal treatment times merely last for periods of up to about 15 minutes, the mechanism's service life has to be correspondingly rated and because the angioplasty catheter is to be used only once, the high technical outlay is justified by the advantages to be achieved by using the angioplasty catheter according to the invention, as described below.

The angioplasty catheter according to the invention can be used to eliminate the disadvantages of the known exogenous ultrasonic systems. Due to the mechanical generation of the sound waves, comparatively large amplitudes and hence very high-energy sound waves can also be endogenously generated. Since the generation of sound waves occurs in direct proximity to the treatment site, only slight energy losses arise, which increases the catheter's effectiveness in removing or disintegrating a stenosis or occlusion. In principle, the use of the catheter according to the invention means that as a result of the influence of the sound waves on the material to be removed, hard and inelastic constituents are ruptured and freed from the composite structure with the vascular wall and disintegrated to the size of the cellular blood constituents. The healthy and elastic constituents, on the other hand, recede. The ultrasound therefore exhibits a selective effect upon the material to be removed. The application of the angioplasty catheter according to the invention consequently reduces the risk of traumatizing the vascular walls, thus permitting more gentle treatment and longer-term treatment successes.

According to another advantageous embodiment feature of the invention, there is provision for the rotor's aforementioned forced guidance to comprise an undulated track disposed at the rotor's two end faces, or to comprise at least a punctiform or linear elevation and an undulated track disposed on the cylindrical housing's inner end faces or to comprise at least a punctiform or linear elevation. When it rotates, the rotor therefore inevitably performs a guided oscillation motion in an axial direction and generates sound waves of a specific frequency and intensity in accordance with the respective speed and track design, i.e. particularly its wave shape and frequency. If in other words a sufficiently large number of elevations evenly distributed over the circumference are located on the aforementioned total of four tracks or if the undulated tracks have a sufficiently large number of elevations and depressions, sound waves which are in the ultrasonic range are produced at a sufficiently high speed. For example, the rotor speed may be 250,000 rpm, the number of axial strokes per rotor revolution may be 5 (five) and a single stroke amplitude may be about 100 µm. These data should of course only be understood as pure reference values and may vary considerably, depending on the particular application.

The shape of a rotor end face's respective track is advantageously adapted to correspond to the shape of a respective track of the cylindrical housing's inner end face opposite this end face. The number and shape of the elevations or the wave shape of the tracks are designed to be geometrically exactly equal and aligned with one another such that when the rotor rotates, the cylindrical housing is deflected in a force-guided manner in an axial direction, i.e. the rotor is guided back into the opposite direction etc. by a pair of tracks toward which the rotor was deflected.

To achieve a specific forced motion of the rotor, it has also proved to be advantageous for the wave shape of the rotor's opposite end faces to be phase-shifted against one another through 180°. By analogy, it is of course also possible for the wave shape of the cylindrical housing's opposite inner end faces to be phase-shifted against one another through 180°. It is usually necessary to presuppose a certain axial freedom of rotor motion, which may depend on the wave amplitude and/or wavelength of the particular wave shape selected.

Another advantageous embodiment of the angioplasty catheter according to the invention provides for the forced guidance to comprise an undulated track disposed at or in the rotor's outer radius and to comprise a guidance member attached to the cylindrical housing's inner radius and engaging with the track. Such a track may for example be designed as a groove in the rotor's outer radius or as a projection or the like extending in an undulated manner around the rotor's outer radius. By analogy, the following version has also proved very positive: in this version, the forced guidance comprises an undulated track disposed at or in the cylindrical housing's inner radius and a guidance member attached to the rotor's outer radius and engaging with the track. The track may in principle be designed in a manner resembling that previously explained for the rotor. Depending on the track design, a guidance member may be formed for example as a punctiform burl which projects into a groovelike track or as a U-shaped claw which punctually engages via a track designed as an undulated projection, or the guidance member may be designed in any other suitable manner. In conjunction with these embodiments, in which a forced guidance is arranged on radial surfaces of the rotor or housing, the rotor and/or the cylindrical housing's inner end faces advantageously have plane-parallel faces.

It has proved to be a particularly beneficial embodiment feature for the rotor's rotary drive to comprise a flexible shaft detachably or nondetachably connected to the rotor. The flexible shaft's rotational motion is preferably generated by a drive located outside the body. The drive is rated such that it can generate a very high speed and sufficient torque. For example, a turbine operated by compressed air or a high-speed electric drive with step-up gear can be used for this purpose. To generate sound, the flexible shaft coupled with the drive supplies the rotational energy to the rotor located at the distal end of the catheter through a lumen specially provided inside the catheter shaft. The connection between the flexible shaft is designed to be torsionally resistant and preferably to be axially loose. In this way, the shaft may for example be connected to the rotor via a suitable elastic adhesive connection.

To cool or lubricate the flexible shaft, it is also advantageous to inject a rinsing fluid and/or medicine, or to remove detached particles and excess fluid by suction, through a lumen situated inside the catheter shaft and designed for receiving the flexible shaft. The catheter shaft advantageously has another lumen so that both processes—rinsing and removal by suction—can also be performed at the same time. At the catheter's proximal end are found the necessary—prior-art—connections for injecting the rinsing fluid, removing detached particles and excess fluids by suction, as well as introducing the guidance wire and a coupling from the flexible shaft to the drive unless the drive is designed as a disposable item and is securely connected to the flexible shaft. The drive itself can be termed prior art.

Various versions have proved to be favorable with regard to the rotor's arrangement or support within the housing located at the distal end of the catheter. In addition to the option of arranging the rotor to be totally centered, there is consequently provision for the rotor to be supported in an eccentrically rotatable manner. Radial oscillations can be generated in a particularly simple manner by means of the rotor's resultant imbalance. Another embodiment according to the invention, however, envisages the rotor being rotatably disposed around an axis in a precessional manner, which results in a similar effect. As to which version preference should be respectively given nevertheless depends to a considerable extent on the particular application.

It has also been shown to be advantageous in the angioplasty catheter according to the invention for the rotor's external diameter to be larger than that of the flexible shaft. Due to the aforementioned very high speeds, the flexible shaft's diameter can be designed not only very thinly so as to transfer a torque to the rotor, but the catheter can also be designed to be extremely flexible across its entire longitudinal extension. During the previously explained catheter movement, the mass concentration—resulting from the rotor's larger diameter with respect to the shaft—at the catheter tip therefore encourages the generation of very high-energy sonic oscillations directly at the treatment site.

According to another advantageous embodiment feature of the invention, the cylindrical housing which surrounds the rotor and which does not co-rotate is coupled via a vibration separation device to the catheter shaft which does not co-rotate either. A vibration separation device in the sense of the invention should be defined as one that connects the housing—which surrounds the rotor and forms the catheter tip—to the catheter shaft such that the catheter tip is able to perform oscillations without being substantially damped by the catheter shaft, or without supplying essential energy thereto as lost energy.

In the angioplasty catheter according to the invention, it has finally proved beneficial in terms of easy handling and the catheter's ability to be introduced even into fairly narrow vessels for the cylindrical housing's external diameter essentially to correspond to that of the catheter shaft.

The object upon which the invention is based is furthermore solved by an inventive method of generating sound waves, particularly ultrasonic waves, within an angioplasty catheter, whereby this method comprises the features of claim 15.

Such a method comprises a step in which at least one rotor that is rotatably disposed within a cylindrical housing at the catheter's distal end and which is force-guided on a predetermined track of motion in an axial and/or radial direction is rotated to generate sound waves, particularly sound waves in the ultrasonic range, in a mechanically endogenous manner as a result of the force-guided motion and to induce a corresponding motion of the housing.

The method according to the invention provides the advantages already explained in conjunction with the angioplasty catheter according to the invention.

Another particularly advantageous embodiment feature of the method according to the invention envisages a step in which the frequency of the generated sound waves is varied by varying the rotor speed. This manner of frequency change is not only very simple but also makes it possible to vary the sound frequency within a specific range. This is particularly significant on the grounds that the consistency of the stenosis or occlusive material may differ greatly, and it may therefore be necessary to apply or vary different frequencies within a specific frequency range during an operation so as to ensure successful treatment.

The invention's exemplary embodiments will be explained in further detail by means of the drawings as follows:

FIG. 1a shows a section through the working end of an only partially represented, inventive angioplasty catheter according to a first embodiment of the invention;

FIG. 1b shows a section through the working end of an only partially represented, inventive angioplasty catheter according to a second embodiment of the invention;

FIG. 2 shows a schematic perspective exploded view of the catheter according to the invention based on FIG. 1a including further details;

FIG. 2a shows a section through the sound generation device according to an embodiment of the invention in which the cylindrical housing is deflected by a rapidly rotating rotor in a force-guided manner in an axial direction;

FIG. 2b shows a section through the sound generation device according to another embodiment of the invention in which the cylindrical housing is deflected by a rapidly rotating rotor in a force-guided manner in an axial and a radial direction;

FIG. 2c shows a section through the sound generation device according to a further embodiment of the invention in which the cylindrical housing is deflected by a rapidly rotating rotor in a radial direction;

To avoid repetitions, identical components will also be identified in the following description and drawings by identical reference numerals unless further differentiation is required.

Figure 3:
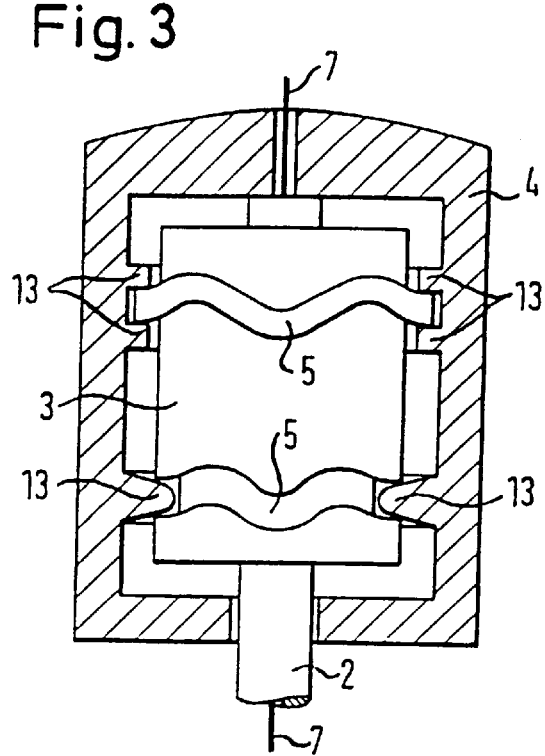
FIG. 3 shows a schematic sectional view of another embodiment of a forced guidance of the rotor of the angioplasty catheter according to the invention.

The distal end of an only partially depicted angioplasty catheter according to a first embodiment of the invention in a schematic sectional view can be inferred from FIG. 1a. The catheter comprises a flexible catheter shaft 1 and a rotor that is rotatably disposed within a cylindrical housing 4 at the distal end of the catheter and force-guided on a predetermined track of motion in an axial and/or radial direction; the rotor comes in the form of an inner cylinder 3 which is connected in a manner secured against rotation with a rotary drive in the form of a flexible hollow shaft 2 projecting through the inner cylinder. The forced guidance is indicated in the drawing by reference numeral 5. When it rotates rapidly, the rotor 3 is used to generate sound waves, particularly sound waves in the ultrasonic range, in a mechanically endogenous manner as a result of the aforementioned forced guidance and to induce a corresponding motion of the housing 4. This will be referred to in even more detail as follows. As can also be identified in FIG. 1a, the cylindrical housing 4 is coupled, in a manner that is non-rigid and does not co-rotate, via a vibration separation device to the catheter shaft 1 which does not co-rotate either. In the present instance, a silicone ring 6 is used as a vibration separation device.

The flexible hollow shaft 2 has a centrically continuous lumen 8 for receiving a guidance wire 7 which extends from the catheter's proximal end to the distal end where it projects through an end-face opening of the housing 4. The catheter can be advanced via this guidance wire 7 to the site of treatment. As well as the guidance wire 7, a rinsing fluid, indicated in the drawing by arrow 11, can be injected through the inner lumen 8 of the flexible shaft 2. The rinsing fluid also serves to cool and lubricate the flexible shaft 2. In the embodiment according to FIG. 1a, the flexible catheter shaft 1 has two openings 9 laterally located at its distal end. Excess fluids and detached particles can be taken in through these openings 9 and then removed to the outside by suction through the duct 10, which is schematically represented by arrow 12.

A second embodiment of the angioplasty catheter according to the invention is depicted in a schematic sectional view in FIG. 1b. This embodiment essentially corresponds to that of FIG. 1a, but the flexible shaft 8 is formed here as a complete shaft and the guidance wire 7 extends eccentrically within a duct 8 specially provided in the catheter wall and device. A rinsing fluid and/or medicine c an also in turn be injected through this duct 8, which is schematically indicated by arrow 11. Similar to FIG. 1a, the openings 9 and duct 10 can also be used in this embodiment for the purpose of removal by suction.

FIG. 2 shows a schematic perspective exploded view of the catheter according to FIG. 1 including further details particularly of the catheter's sound generation components. The sound generation device shown in FIG. 2 essentially comprises the inner cylinder 3 which is centrically attached to the distal end of the flexible shaft 2 and to the cylindrical housing 4 that surrounds this inner cylinder 3 and which, as already mentioned above, is secured to the catheter shaft 1 in a manner that is non-rigid and does not co-rotate. The rotatable inner cylinder 3 has an undulated track 5.1 at its two end faces. An undulated track 5, the shape of which corresponds to the respectively opposite undulated track 5 of the inner cylinder 3, is also situated at both inner end faces of the cylindrical housing 4.

The rotational energy for the inner cylinder 3 is generated by a drive located outside the body and not depicted in further detail; this energy is guided to the inner cylinder 3 by means of the flexible shaft 2 through the lumen 10 within the flexible catheter shaft 1. The inner cylinder 3 secured to the distal end of the flexible shaft 2 therefore also performs the rotational motion. When the inner cylinder 3 rotates, it is deflected in a force-guided manner in an axial direction every time two elevations of the undulated tracks 5—from the inner cylinder 3 and the cylindrical housing 4—face one another. If a sufficiently large number of elevations evenly distributed over the circumference are located on the tracks 5 or if the speed of the inner cylinder 3 is sufficiently high, there arise sound waves which mainly lie in the ultrasonic range. The rotating inner cylinder 3 as a result of the force-guided motion induces a corresponding motion of the housing 4.

For example, the speed of the inner cylinder 3 may be about 250,000 rpm, the number of axial strokes generated by the undulated tracks 5 per rotor revolution may be five and a single stroke amplitude may be about 100 $\mu$m. These data should only be understood as pure reference values and may vary considerably depending on the particular application. The speed of the inner cylinder 3 is varied so as to vary the frequency of the sound waves generated.

Instead of the wave shape of the tracks 5, punctiform or linear elevations on otherwise planar end faces of cylinder 3 and housing 4 can also be used. The effect is the same as in the previously described undulated tracks 5.

The sound generation device depicted in FIG. 2 can also in principle be used for the version according to FIG. 1b, thus rendering further explanations unnecessary.

Three embodiments of the sound generation device are listed in FIGS. 2a to 2c.

The sound generation device depicted in FIG. 2a corresponds to the one already discussed in conjunction with FIGS. 1a and 2.

Another embodiment of the invention is portrayed in FIG. 2b. What distinguishes it from the embodiment according to FIG. 2a is that the inner cylinder 3 used for sound generation is eccentrically attached to the distal end of the flexible shaft 2. When the inner cylinder 3 rotates, it and hence the catheter tip are consequently deflected not only in an axial direction but also in a radial direction.

FIG. 2c shows a further embodiment of the invention. Unlike the embodiment portrayed in FIG. 2a, the inner cylinder 3 is eccentrically attached to the distal end of the flexible shaft 2 and has plane-parallel faces. The inner end faces of the cylindrical housing 4 are likewise plane-parallel in this embodiment. When the inner cylinder 3 rotates, vibrations are generated by the imbalance.

FIG. 3 shows a schematic sectional view of another embodiment in which the forced guidance of the inner cylinder 3, which acts as a rotor, is implemented by an undulated track 5 disposed at or in the outer radius of the inner cylinder 3 and by a guidance member 13 attached to the inner radius of the cylindrical housing 4 and engaging with the track 5. On the one hand, the undulated track 5 can be designed as an undulated groove 5 and the guidance member 13 as a punctiform elevation 13 protruding into the groove, while on the other, the undulated track 5 can be designed as an undulated projection 5 and the guidance member 13 as a claw 5 or the like which encompasses this projection 5. In principle, these two modifications may also be envisaged at the same time, provided their wave shape is in phase.

Figure 4:
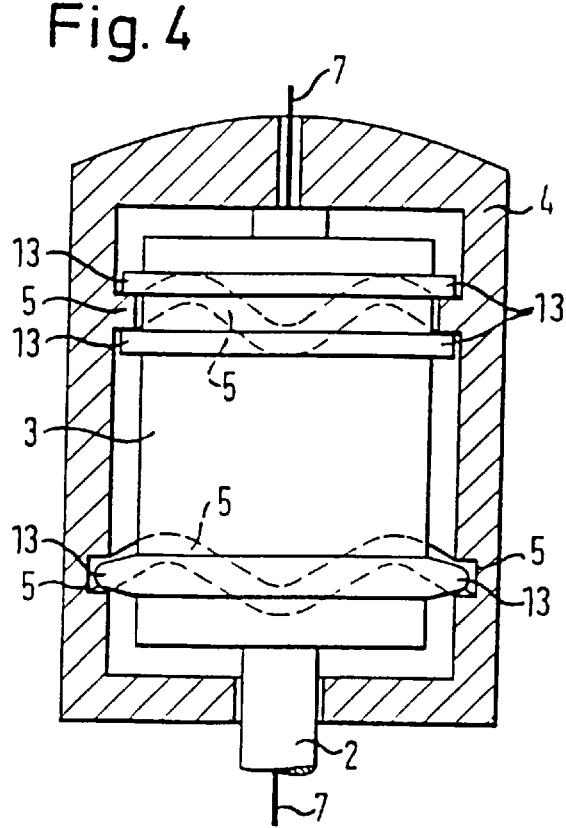
FIG. 4 shows a schematic sectional view of another embodiment of a forced guidance of the rotor of the angioplasty catheter according to the invention.

Finally, FIG. 4 shows a schematic sectional view of a further embodiment of the catheter according to the invention in which the forced guidance of the inner cylinder 3, which acts as a rotor, is implemented by an undulated track 5 arranged at or in the inner radius of the cylindrical housing 4 and by a guidance member 13 attached to the outer radius of the rotor 3 and engaging with the track 5. On the one hand, the undulated track 5 of the cylindrical housing 4 can be designed as an undulated groove 5 and the guidance member 13 as a punctiform elevation 13 projecting into the groove, while on the other, the undulated track 5 can be designed as an undulated projection 5 and the guidance member 13 as a claw 5 or the like encompassing this projection 5. In principle, these two modifications may also be envisaged at the same time, provided their wave shape is in phase.

The present invention is not restricted to the exemplary embodiments described above. On the contrary, the angioplasty catheter according to the invention may vary considerably from the aforementioned versions, depending on the particular application.

Reference numerals in the claims, description and drawings merely serve to improve comprehension of the invention and are not intended to limit the extent of protection.

List of reference numerals

The following are designated:
1 Catheter shaft
2 Flexible shaft
3 Inner cylinder (rotor)
4 Cylindrical housing
5 Punctiform or linear elevations
5.1 Undulated track
5.2 Undulated track
6 Silicone ring
7 Guidance wire
8 Lumen
9 Openings
10 Duct
11 Rinsing fluid
12 Excess fluid or detached particles
13 Guidance member

We claim:

1. An angioplasty catheter having a distal end, comprising:
   a housing positioned at the distal end of the catheter;
   a rotor rotatably disposed in the housing;
   a force-guide connected to the housing and positioned to contact the rotor as the rotor rotates, the force-guide being responsive to the rotational motion of the rotor to induce a guided oscillatory axial movement of the housing and thereby generate ultrasonic waves.

2. The angioplasty catheter of claim 1, wherein the rotor has proximal and distal faces and wherein the force-guide comprises an undulated track which contacts the proximal and distal rotor faces.

3. The angioplasty catheter of claim 1, wherein the force-guide comprises an undulated track.

4. The angioplasty catheter of claim 3, wherein the undulated track includes a top track and a bottom track, the top and bottom tracks being axially spaced apart.

5. The angioplasty catheter of claim 4, wherein the undulations in the top and bottom tracks are in phase.

6. The angioplasty catheter of claim 1, further comprising a vibration separator interposed between the housing and the catheter.

7. The angioplasty catheter of claim 6, wherein the vibration separator is a silicone ring.

8. The angioplasty catheter of claim 1, further comprising an elongate flexible rotor drive shaft disposed within the angioplasty catheter and connected to the rotor to drive the rotor.

9. The angioplasty catheter of claim 8, wherein the flexible rotor drive shaft is hollow.

10. The angioplasty catheter of claim 8, wherein the flexible rotor drive shaft includes a first lumen for supplying one of a rinsing fluid and medicine and a second lumen for suck one of excess fluid and detached particles.

11. The angioplasty catheter of claim 8, wherein said rotor has a greater diameter than said flexible rotor drive shaft.

12. The angioplasty catheter of claim 1, wherein said rotor is positioned eccentrically within the housing.

13. The angioplasty catheter of claim 1, wherein the catheter includes an eccentric duct sized to receive a guidance wire.

14. The angioplasty catheter of claim 1, wherein said rotor is encased in the housing such that no rotational motion is transferrable to the biological tissue.

* * * * *